United States Patent [19]

Flanner

[11] 4,234,567

[45] Nov. 18, 1980

[54] WASP AND HORNET SPRAY COMPOSITION

[76] Inventor: Lloyd T. Flanner, 4175 Americana Dr., Apt. A-12, Stow, Ohio 44224

[21] Appl. No.: 1,706

[22] Filed: Jan. 8, 1979

[51] Int. Cl.³ .................... A61L 9/04; A01N 37/00; A01N 37/08; A01N 43/02
[52] U.S. Cl. .................... 424/45; 424/DIG. 10; 424/278; 424/306
[58] Field of Search .................... 424/45, 10

[56] References Cited

U.S. PATENT DOCUMENTS

| | | | |
|---|---|---|---|
| 3,644,645 | 2/1972 | Bordence et al. | 424/DIG. 10 |
| 3,873,725 | 3/1975 | Skinner et al. | 424/DIG. 10 |
| 3,947,567 | 3/1976 | Berg, Jr. et al. | 424/45 |
| 3,966,963 | 6/1976 | Okuno et al. | 424/45 X |
| 3,970,584 | 7/1976 | Hart et al. | 424/45 X |
| 3,996,153 | 12/1976 | Heeb et al. | 424/45 |
| 4,134,968 | 1/1979 | Stebles et al. | 424/45 |

*Primary Examiner*—Dale R. Ore
*Attorney, Agent, or Firm*—Vern L. Oldham

[57] ABSTRACT

A wasp and hornet spray composition formed from known insecticides including pyrethrins, piperonyl butoxide, carbaryl, petroleum distillates and inert ingredients is provided with a solvent and propellant composition consisting of 1,1,1 trichloroethane and carbon dioxide and wherein a synergistic action is obtained between the solvent-propellant and the insecticides to improve the effectiveness thereof.

3 Claims, No Drawings

WASP AND HORNET SPRAY COMPOSITION

BACKGROUND OF INVENTION

Heretofore there have been many different types of insecticides put out commercially, and many of such insecticides have substantially the same insecticide components therein and with many commercial compositions also using very similar or the same inert ingredients. Many of these compositions, as available today, are propelled by various types of fluorocarbons.

As is well known, the use of fluorocarbons is objectionable to many scientists and environmentalists and some appreciable pollution dangers apparently exist by use of these materials.

The use of carbon dioxide as a propellant gas has been proposed heretofore, and one U.S. Pat. No. 3,387,425 has been issued on a process for dissolving carbon dioxide in solvents.

OBJECTS OF THE INVENTION

The objects of the invention are to provide a novel and improved wasp and hornet spray composition and especially one that avoids the use of fluorocarbon as a propellant.

Another object of the invention is to propel or dispense insecticide compositions more effectively by use of carbon dioxide gas and to use 1,1,1 trichloroethane as a solvent material in the composition, which solvent aids in causing penetration of the active ingredients of the composition into hornets nests, porous objects, and the like for deposit of the active ingredients therein to avoid reinfestation of such objects by the insects.

Yet another object of the invention is to improve the efficiency and functioning of wasp and hornet sprays and such result has been achieved, unexpectedly, by a synergistic effect obtained by the use of 1,1,1 trichloroethane as a solvent and carbon dioxide gas as a propellant in combination with known insecticide compositions the effectiveness of which has been improved by use of the particular solvent-propellant composition of the invention.

The foregoing and other objects and advantages of the invention will be made more apparent as the specification proceeds.

SUBJECT MATTER OF INVENTION

The invention, as one embodiment thereof, relates to the combination of known ingredients of wasp and hornet spray compositions with a propellant and solvent system widely different from that currently used in commercial products; and which system consists of 1,1,1 trichloroethane and carbon dioxide gas, used in about 50% by weight parts in combination with about 50% parts by weight of known wasp and hornet insecticides and normally comprising the active ingredients of pyrethrins, piperonyl butoxide, and cabaryl combined with substantial quantities of petroleum distillates and inert ingredients.

Specifically, in practice of the present invention, a wasp and hornet spray composition has been prepared that consists of the following ingredients in the proportions indicated:

| | | |
|---|---|---|
| Pyrethrins | .075 | Parts by weight |
| Piperonyl Butoxide | .188 | " |
| Carbaryl | .500 | " |
| Petroleum Distillates | 24.222 | " |
| Inert Ingredients | 25.015 | " |
| 1,1,1 Trichloroethane | 46.250 | " |
| Carbon Dioxide | 3.750 | " |
| | 100.000 | |

In this composition, the pyrethrins, piperonyl butoxide and carbaryl are the active ingredients in combination with the petroleum distillates. The piperonyl butoxide used was of the technical grade, and the carbaryl is 1-naphthyl N-methylcarbamate.

Petroleum distillates are known materials in the trade and they normally comprise odorless mineral spirits, naptha, high aromatic naptha or other aliphatic solvents commonly used in insecticides as solvents. The inert ingredients will vary with the different solvents used in the compositions, but normally it means that fraction of petroleum distillates that doesn't function as an insecticide nor as an active solvent for insecticide ingredients.

In making up the composition, the propellant, carbon dioxide, can be added at any time and in any way as is conventional in the trade. The carbon dioxide could be dissolved in the 1,1,1 trichloroethane in accordance with the teachings of U.S. Pat. No. 3,387,425, if desired. The solvent material and the propellant system preferably use trichloroethane that has been saturated with carbon dioxide gas. Such saturation is achieved with 3.75% carbon dioxide by weight in the composition as indicated hereinabove. If a separate solvent-propellant system is prepared, of course at that time the percentages or parts by weight of the propellant and solvent would be doubled to provide a 100% parts by weight composition and then 50 parts by weight of such composition would be used in association with 50 parts by weight of the insecticide or pesticide component mixture of the composition.

In other compositions made in accordance with the invention, it has been found that the carbon dioxide gas might go down as low as about 1% of the composition, and that if one tried to put or use 5% carbon dioxide in the system, that was too much and it would not be used efficiently.

In normal practice in the insecticide-pesticide industry, the active ingredients listed hereinabove normally do not go any lower than the percent or parts by weight as stated.

In the present invention, a very unusual and unobvious result has been achieved, i.e. a higher kill factor or kill ratio has been obtained by the composition of the invention than is obtained by equivalent insecticide compositions using other propellant-solvent systems whereby it is believed that a synergistic effect has been obtained by use of the propellant-solvent system of the invention. It also has been found and determined that because of the solvent action of the 1,1,1 trichloroethane used, this causes penetration of the active ingredients into wasp nests, porous structures and other areas for deposit to prevent reinfestation of such structures by the undesired wasps or other insects.

In various tests conducted with compositions of the invention, its superiority in killing wasps and hornets is made more evident. For example, in the following test, the aerosols of the invention were used in those identified as 192A and 192. The compositions 192B are commercial compositions as available today both the insecticide composition and spray and solvent systems being of known commercial types. The nozzle on the 192A types was different from those on the other aerosol containers and appeared to give a controlled stream with better directional control. This following test was conducted in a room in an old broken down house against the paper-nest wasp which is known as Polistes fuscatus aurifer:

Data:

| Aerosol | Nest Size | No. Pupal Cells 6/21 | 6/29 | 7/25 | Spray Duration | Gm. Spray Emitted | No. Adult Wasps Pre-Spray | Knocked Down | Control |
|---------|-----------|------|------|------|----------------|-------------------|---------------------------|--------------|---------|
| 192A | 5"diam | 92 | 92 | 92 | 2 sec. | 30 | 38 | 38 | 100 |
| 192B | 3"diam | 37 | 44 | 19 | 2 sec. | 9 | 18 | 9 | 50 |
| 192 | 1"diam | 4 | 2 | 2 | 1.5 sec. | 3 | 5 | 5 | 100 |

Observations:

1. With ETN 192A knockdown was instantaneous with all of the 38 wasps falling straight down and none flying off. Upon hitting the ground, they were fairly immobile and all signs of movement ceased within 5 minutes.

2. With ETN 192B knockdown was poor with only one wasp falling straight down. Many flew out the broken windows with only 9 being recovered from the floor of this 12 ft. by 8 ft. room. Seven of the 9 although immobilized exhibited considerable leg and stinger movement for 3 hours. Eight days after treatment 2 live wasps were on the nest and it was considered again active.

3. With ETN 192 knockdown was almost equal to 192A with all wasps falling to the ground in a 4 ft. circle beneath the nest. Upon hitting the ground, they were immobile and all signs of movement ceased within 5 minutes.

Conclusions:

1. Both ETN 192A and ETN 192 were decidedly superior to ETN 192B against the golden paper wasp (P. fuscatus aurifer).

2. Knockdown with the two new aerosols was immediate unlike ETN 192B where the applicator was definitely in danger of being stung by survivors.

3. Regarding residual control, 192A apparently prevented emergence of any developing pupae; 192 allowed 2 of 4 to emerge; while 192B did not inactivate the nest allowing future oviposition and adult emergence.

In test Trial No. 1 referred to hereinabove, the test involved three active nests that were located in an abandoned wood-frame house where all windows were broken and these nests were 12 to 20 ft. apart. Each nest was sprayed from about a distance of 2 ft. for a duration of about 1.5 to 2.0 seconds. It was raining outside and hence was assumed that all of the adult wasps were on the nests. Wasps were counted on the nests just prior to spraying and those knocked down were counted. The nests were also measured and the number of pupal cells counted to measure later emergence.

In the second test involving both paper-nest wasps and mud-dauber wasps (Sphecius spp), the following tests data was obtained when the test aerosols as indicated hereinabove were used against 11 to 16 wasps that had been freshly caught and were released in an enclosed room for test purposes. Each wasp, usually located on a vertical window screen, received as many short bursts of the aerosol as necessary to cause knockdown of such wasps. The spray distance was approximately 2 ft. from the target. The knocked-down wasps were further observed to determine duration until death or complete immobility occurred. Such tests were as follows:

TABLE 1

(Trial 2)

| Aerosol | Wasp No. | No. Spray Bursts for Knock Down | Time For Knockdown | Death or full Immobility Within 5 min. | 10 min. | 15 min. |
|---------|----------|-------------------------------|--------------------|----------------------------------------|---------|---------|
| 192A | 1 | 1 | 1 sec. | + | | |
| | 2 | 3 | 4 | + | | |
| | 3 | 2 | 2 | + | | |
| | 4 | 2 | 2 | + | | |
| | 5 | 3 | 4 | + | | |
| | 6* | — | 8 | | + | |
| | 7** | 1 | 1 | | + | |
| | 8 | 3 | 4 | + | | |
| | 9** | 4 | 8 | | + | |
| | 10 | 3 | 3 | + | | |
| | 11 | 1 | 1 | + | | |
| | | 23 = 75 gm spray | | | | |
| 192 | 1 | 3 | 4 | + | | |
| | 2 | 4 | 6 | + | | |
| | 3* | — | 8 | + | | |
| | 4* | — | 8 | + | | |
| | 5 | 2 | 2 | + | | |
| | 6 | 2 | 2 | + | | |
| | 7 | 3 | 4 | + | | |
| | 8 | 3 | 4 | + | | |
| | 9 | 2 | 3 | + | | |
| | 10** | 2 | 2 | + | | |
| | 11** | 5 | 6 | | + | |
| | 12* | — | 10 | | + | |
| | | 26 = 45 gm spray | | | | |
| 192B | 1 | 6 | 8 | | + | |
| | 2 | 5 | 7 | | + | |
| | 3 | 2 | 4 | + | | |
| | 4 | 4 | 6 | | + | |
| | 5 | 3 | 5 | | + | |
| | 6 | 3 | 5 | | + | |
| | 7 | 4 | 5 | | + | |
| | 8 | 4 | 5 | | | + |
| | 9 | 6 | 9 | | + | |
| | 10 | 11 | 12 | | + | |
| | 11** | 4 | 6 | | | + |
| | 12 | 5 | 7 | | | |
| | 13 | 9 | 10 | | + | |
| | 14 | 5 | 7 | | | |
| | 15 | 6 | 8 | | + | |
| | 16 | 9 | 12 | | + | |
| | | 83 = 60 gm spray | | | | |

*Wasp within 6" of another wasp receiving direct hit and knocked down from drift
**Polistes wasp; all others were mud daubers Conclusions:

1. Both ETN 192A and ETN 192 were far superior to ETN 192B for knockdown of mud-dauber wasps simply because fewer spray blasts were necessary to achieve knockdown.

2. ETN 192A was better than ETN 192 because wasp immobility occurred sooner thus lessening the possibility of the applicator being stung.

In yet a further test conducted on the compositions of the invention, captive wasps were placed in a cylindrical plastic screen cage that was placed on an outdoor bench and sprayed from a distance of 6 ft. for about 2 seconds. Knockdown time, duration from spray impact to when the insect was off its feet was recorded for each species. Time of death (no sign of movement) was also recorded.

It should be noted that the spray range of the test specimen 192 and 192B was about 6-7 ft., while that of the 192A was 9-10 ft. The test results were as follows:

TABLE 2

| Aerosol | Gm Used | Wasp species | (Trial 3) No. Wasps /Cage | Average Time Knockdown | Death | Test Date |
|---|---|---|---|---|---|---|
| 192 | 9 | V. maculifrons | 5 | 114 sec. | 40 min. | 7/23 |
| | | Sphecius spp. | 2 | 80 sec. | 50* min. | 7/23 |
| | 10 | P. fuscatus aurifer | 3 | 12 sec. | 30* min. | 7/23 |
| | 12 | P. macaensis | 2 | 190 sec. | 60* min. | 7/24 |
| 192A | 24 | V. maculifrons | 5 | 6 sec. | 21 min. | 7/23 |
| | | Sphecius spp. | 2 | 7 sec. | 20 min. | 7/23 |
| | 26 | P. fuscatus aurifer | 3 | 20 sec. | 30* min. | 7/23 |
| | 22 | P. macaensis | 2 | 70 sec. | 10 min. | 7/24 |
| 192B | 7 | V. maculifrons | 5 | 480 sec. | 50 min. | 7/23 |
| | | Sphecius spp. | 2 | 30 sec. | 11 min. | 7/23 |
| | 10 | P. fuscatus aurifer | 3 | 143 sec. | 50* min. | 7/24 |
| | 8 | P. macaensis | 2 | 290 sec. | 50* min. | 7/24 |

*Wasp still convulsing at this time.

Conclusions:
1. Against yellow jackets, mud-daubers, and paper-nest wasps, ETN 192A is definitely the candidate of choice since knockdown was swiftest and eventual death faster than ETN 192 or ETN 192B.

2. ETN 192A does deliver more toxicant in a given time period and its effective range is superior. In addition, its spout nozzle not only directs the spray pattern better but the applicator is less likely to miss the target with this nozzle design.

3. ETN 192 and ETN 192B have approximately the same amount of delivery; however, the former is superior for knockdown for these two materials.

Somewhat similar tests were conducted in relation to ordinary houseflies (Musca domestica L.). Again, the spray compositions of the invention as evidenced hereinabove were much more effective and had greater kill ratio than standard commercial compositions using the same pesticide ingredients but with different solvent and spray systems, usually fluorocarbons.

It should be appreciated that in practice of the invention, any desired type of insecticide composition can be used and thus in some instances, it is considered that one would just refer to a pretroleum distillate presence in the composition of around 49 to 49.5% and these could be considered part of the active ingredients. However, the inert ingredients are quite similar to the petroleum distillates considered part of the active ingredients as indicated hereinabove. But, such inert ingredients may vary as indicated hereinabove.

By the foregoing tests, it is believed that the unobvious superiority and synergistic effect obtained by the composition of the invention has been established. The composition functions under normal operating conditions and meets all commercial and government requirements insofar as I am aware.

Hence, it is believed that the objects of the invention have been achieved and that a more efficient, effective, improved spray composition for immobilizing and killing wasps, hornets, houseflies and similar insects has been provided by the invention.

While one complete embodiment of the invention has been disclosed herein, it will be appreciated that modification of this particular embodiment of the invention may be resorted to without departing from the scope of the invention.

What is claimed is:

1. A wasp and hornet spray composition formed from about 50% of a mixture of pyrethrins, piperonyl butoxide, carbaryl, petroleum distillates and inert ingredients and about 50% of a propellant solvent composition consisting of 1,1,1 trichloroethane and carbon dioxide; there being a synergistic action obtained between the 1,1,1 trichloroethane and the active ingredients of pyrethrins, piperonyl butoxide, carbaryl and petroleum distillate which are present in about 0.075; 0.188; 0.500 and 24.222 parts by weight, respectively, and where about 25 parts by weight of inert ingredients are present in the complete spray composition, and where about 7.5 parts of carbon dioxide are dissolved in about 92.5 parts of the 1,1,1 trichloroethane to form the spray-solvent mixture.

2. A wasp and hornet spray as in claim 1 and where the 1,1,1 trichloroethane is saturated with carbon dioxide to form the propellant for the spray.

3. A wasp and hornet spray composition as in claim 2 where said propellant will penetrate into porous structures and wasp nests and deposit ingredients therein to prevent reinfestation of the nests by wasps or hornets.

* * * * *